US006426182B1

(12) United States Patent
Carrico

(10) Patent No.: US 6,426,182 B1
(45) Date of Patent: Jul. 30, 2002

(54) APPARATUS AND METHOD FOR DETERMINING WHETHER FORMALDEHYDE IN AQUEOUS SOLUTION HAS BEEN NEUTRALIZED

(75) Inventor: Robert J. Carrico, Elkhart, IN (US)

(73) Assignee: Serim Research Corporation, Elkhart, IN (US)

( * ) Notice: Subject to any disclaimer, the term of this patent is extended or adjusted under 35 U.S.C. 154(b) by 0 days.

(21) Appl. No.: 09/510,713

(22) Filed: Feb. 22, 2000

(51) Int. Cl.$^7$ ............................ C12Q 1/00; G01N 33/53
(52) U.S. Cl. ............................ 435/4; 435/975; 435/970
(58) Field of Search ............................ 435/4, 975, 970

(56) References Cited

U.S. PATENT DOCUMENTS

| | | | |
|---|---|---|---|
| 3,909,408 A | * 9/1975 | Ishida et al. | 435/4 |
| 3,945,798 A | * 3/1976 | Young | 435/4 |
| 4,563,422 A | 1/1986 | Deneke et al. | 435/27 |
| 4,810,633 A | 3/1989 | Bauer et al. | 435/25 |
| 5,545,336 A | * 8/1996 | Wheeler et al. | 435/4 |

OTHER PUBLICATIONS

Aldrich Technical Information Bulletin No. AL–145, PRU-PALD, Aldrich Chemical Company, Inc., Milwaukee, WI (1993).
"Quantitative Analysis of Formaldehyde", pp. 483–488 (1963).
"Experiment 11, The Fuchsin–Aldehyde Reagent", The Systematic Identification of Organic Compounds, Shriner, Fuson and Curtin, Fourth Edition, pp. 14–15(1942).
"Experiment 23, Sodium Bisulfite Solution", The Systematic Identification of Organic Compounds, Shriner, Fuson & Curtin, Fourth Edition, pp. 149–150; and "Experiment 24, Sodium Hydroxide Solution", pp. 150–151(1962).
"Appendix III", Buffers for pH and Metal Ion Control, D.D. Perrin and Boyd Dempsey, pp. 156–163 (1974).
"Oxidation–Reduction Potentials of Organic Systems", W. Mansfield Clark, pp. 130–133, 402–411, and 402–423 (1960).
"The Sigma–Aldrich Handbook of Stains, Dyes and Indicators", Floyd J. Green, Aldrich Chemical Company, Inc., pp. 255, 405–406, and 703–704 (1990).

"Increasing Sensitivity of 3–Methyl–2–Benzothiazolone Hydrazone Test for Analysis of Aliphatic Aldehydes in Air", Analytical Chemistry, vol. 36, No. 3,(Mar. 1964) pp. 679–681.
"Formaldehyde", J. Frederic Walker, American Chemical Society Monograph Series, Third Edition, pp. 251–252 (1969).
"Aldehydes and Ketones", Chemistry of Organic Compounds, Carl R. Noller, Second Edition, pp. 201–202 (1957).
Handbook of Chemistry and Physics, Robert C. Weast, 52nd Edition, pp. D–113 and D–121 (1971).
"Tissue–Tek NEUTRA–GUARD Aldyhyde Control System", Tissue–Tek Proven Reliability, Sakura, http://www.sakuraus,com/ (1963).
"PURPALD", U.S. Trademark Registration No. 0,955,548, issued on Mar. 20, 1973.
"NEUTRALESX", U.S. Trademark Registration No. 2,189,343, issued on Sep. 15, 1998.
TISSUE_TEK, U.S. Trademark Registration No. 0,743,380, issued on Jan. 8, 1963.
SCIGEN NEUTRALEX, Certification No.: 97–01–024, issued by the State of California, Environmental Protection Agency; (1993).

* cited by examiner

*Primary Examiner*—Louise N. Leary
(74) *Attorney, Agent, or Firm*—Baker & Daniels

(57) ABSTRACT

A test device, method, and indicators for the colorimetric determination of formaldehyde neutralization in an aqueous solution initially containing formaldehyde are provided. Formaldehyde is neutralized by reaction with sulfite ion, where the sulfite ion is provided by dissolving a sulfite-containing compound or neutralizer, such as sodium sulfite, sodium bisulfite, or a mixture thereof, into the aqueous solution containing formaldehyde. The indicators may include dyes capable of exhibiting a color change in the presence of an excess amount of sulfite ion over the amount of formaldehyde in the aqueous solution. A test medium includes the dye, where the test medium may be a test strip impregnated with one of the indicator dyes and optionally a buffer, or a liquid solution containing the dye. The test medium may be contacted with the formaldehyde-containing solution to indicate the neutralization of formaldehyde by exhibiting the color change in the presence of excess sulfite ion, providing a user with a confirmation that the formaldehyde in the solution has been neutralized.

57 Claims, No Drawings

APPARATUS AND METHOD FOR DETERMINING WHETHER FORMALDEHYDE IN AQUEOUS SOLUTION HAS BEEN NEUTRALIZED

BACKGROUND OF THE INVENTION

1. Field of the Invention

The present invention relates to disposal of wastes containing formaldehyde, and more particularly to a test device, method, and indicators for confirming the neutralization of formaldehyde by the calorimetric determination of excess formaldehyde neutralizer in aqueous solution.

2. Description of the Related Art

Formaldehyde is used in a wide variety of industrial and laboratory applications. Disposal of formaldehyde waste through sewer systems is inexpensive and convenient because formaldehyde is very soluble in water and is degraded by a variety of microorganisms. However, because formaldehyde is toxic, disposal of wastes containing formaldehyde requires special procedures.

The United States Environmental Protection Agency (EPA) regulations require that solutions containing formaldehyde are neutralized before being disposed into a sewer system. More specifically, the EPA requires neutralized formaldehyde solutions to be tested to verify that residual formaldehyde is below 10 ppm and that the pH is in the neutral range 6.0 to 8.0.

The safest and most practical commercial method for the neutralization of formaldehyde is by exposure of formaldehyde to sulfite ion, usually by adding sodium sulfite, sodium bisulfite, or a mixture thereof to the aqueous solution containing formaldehyde. The reactions of formaldehyde with sodium sulfite and sodium bisulfite, respectively, are the following equilibrium reactions:

(Sodium sulfite)

and

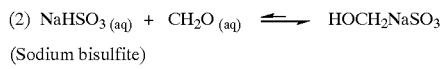

(Sodium bisulfite)

whereby sodium sulfite and sodium bisulfite each react with formaldehyde to yield sodium formaldehyde bisulfite ($HOCH_2NaSO_3$), a very stable compound in aqueous solution. The equilibrium for this reaction is shifted strongly to the right (towards the formation of sodium bisulfite formaldehyde) and the relative concentrations of sulfite ion and the free formaldehyde in the solution are very low after the reaction which forms sodium bisulfite formaldehyde.

Known methods for the determination of whether formaldehyde has been neutralized in an aqueous solution have been directed toward the direct detection or measurement of the amount of free formaldehyde in the solution, and have proven problematic for several reasons. Several prior known methods are impractical and difficult to use, such as several qualitative methods for determining formaldehyde in aqueous solutions described in Walker, J. F., *Formaldehyde*, 3$^{rd}$ ed., 483–488 (1964). For example, one such method is to measure the specific gravity and refractivity of the solution, and then estimate the formaldehyde content of the solution from those measurements using a ternary diagram, such as that described in Natta, G., Baccaredda, M., *Giorn. chim. ind. applicata*, 15, 273–81 (1933). This method is not useful from a practical standpoint, as it requires the measuring of both the specific gravity and refractivity of the solution, yields only an estimate of formaldehyde concentration, is cumbersome to perform in the laboratory, and is only effective for pure aqueous formaldehyde solutions, or aqueous formaldehyde solutions containing only a very small percentage of impurities.

A more accurate method of determining formaldehyde in aqueous solutions is the sodium sulfite titration method, described by Walker, pp. 486–488. While useful in the analytical laboratory for determining the concentration of formaldehyde in aqueous solution, the sodium sulfite titration method is cumbersome to perform, both in large scale and in small scale disposals, as a qualitative method of determining whether aqueous solutions of formaldehyde have been neutralized. The sodium sulfite titration method is also time-consuming to perform, and may require multiple titrations.

Other qualitative calorimetric tests for the direct determination of formaldehyde are disadvantageous because they require acidic conditions. The accuracy of these methods is questionable, because the sodium bisulfite formaldehyde product, while stable in neutral conditions, becomes unstable in acidic conditions and decomposes to form free formaldehyde and sulfurous acid. Noller, C. R., *Chemistry of Organic Compounds*, 2$^{nd}$ ed., 201–202 (1957). Not surprisingly, these types of tests do not give meaningful results.

For example, a prior known method for the determination of formaldehyde in acidic conditions involves reacting formaldehyde with 3-methyl-2-benzothiazolone hydrazone (MBTH), followed by oxidizing the resulting adduct with ferric chloride in 1.6% sulfamic acid. Hauser, T. H. and Cummins, R. L., *Anal. Chem.* 36, 679–681 (1964). Sulfamic acid is a strong acid that will disrupt the sodium bisulfite formaldehyde complex to yield free formaldehyde, as noted by Noller, p. 202. In addition, any excess sulfite/bisulfite present in the neutralized formaldehyde solution reduces the ferric chloride and blocks the oxidation of the MBTH/formaldehdye adduct. As a result, this method is ineffective for the determination of whether formaldehyde has been neutralized with sodium sulfite/bisulfite in an aqueous solution.

Another known method for the determination of formaldehyde in acidic conditions involves the reaction of Fuchsin, a pink triphenylmethane dye, with sulfurous acid to yield the colorless leucosulfonic acid, also known as "Schiffs reagent." Schiffs reagent is unstable, and reacts with aldehydes to form a violet-purple quinoid dye, known as the Fuchsin-aldehyde reagent. Shriner, R. L., Fuson, R. C., and Curtin, D. Y., *The Systematic Identification of Organic Compounds*, 4$^{th}$ ed., 114–115 (1956). The colored Fuchsin-aldehyde reagent is not useful for the determination of formaldehyde because, as described above, the acidic conditions needed for the assay disrupt the sodium bisulfite formaldehyde complex to yield free formaldehyde. Noller, pp.201–202; Shriner et al., pp.149–150.

Still other qualitative calorimetric methods for the direct determination of formaldehyde are disadvantageous because they require alkaline conditions. Similar to acidic conditions, alkaline conditions also affect the stability of sodium bisulfite formaldehyde. For example, one test for the direct determination of formaldehyde uses 4-amino-3-hydrazino-5-mercapto-1,2,4-triazole, supplied under the commercial name Purpald® by Sigma-Aldrich Co., Inc., (Purpald® is a registered trademark of Aldrich Chemical Co., Inc.) or a variant of this compound, as a calorimetric indicator in alkaline solution. This test is supplied by Sakura Finetek U.S.A., Inc. under the commercial name Tissue-Tek® NEUTRALEX™ Aldehyde Test Kit. (NEUTRALEX™ is a registered trademark of Scigen, and Tissue-Tek® is a registered trademark of Sakura Finetechnical Co., LTD). In this test, the 4-amino-3-hydrazino-5-mercapto-1,2,4-triazole reacts with aldehydes, and is oxidized by oxygen in air to yield a purple-to-magenta-colored 6-mercapto-s-triazolo-[4,3-b]-s-tetrazine, as described in Technical Information Bulletin Number AL-145 from Aldrich Chemical Co. (citing Dickinson, R. G., Jacobsen, N. W., *Chem. Commun.*, 1719 (1970)). As demonstrated in Example I and described below, this assay is of doubtful utility.

First, the strong alkaline conditions necessary for the 4-amino-3-hydrazino-5-mercapto-1,2,4-triazole to react with aldehydes adversely affect the stability of sodium bisulfite formaldehyde, such that the assay result is not indicative of the actual amount of free formaldehyde present in the test solution.

In addition, as demonstrated in Example I, the Tissue-Tek® test strips indicate relatively low formaldehyde levels in standard solutions actually known to have relatively high levels of formaldehyde. It is believed that the sulfite ion in the aqueous solution blocks the oxidation of the formaldehyde/4-amino-3-hydrazino-5-mercapto-1,2,4-triazole adduct which is required to form the purple-to-magenta colored triazine.

Furthermore, in solutions with relatively low formaldehyde levels, consumption of the small amount of free formaldehyde by the colorimetric indicator causes the equilibrium between free formaldehyde and sodium bisulfite formaldehyde to shift to the left, that is, away from the formation of sodium bisulfite formaldehyde and toward the formation of more free formaldehyde. Problematically, this type of colorimetric test can consume a relatively large fraction of the free formaldehyde in a solution that contains relatively low formaldehyde levels initially, such as near the EPA requirement of 10 ppm or less. Eventually, the reversible equilibrium will allow as much of the formaldehyde in sodium bisulfite formaldehyde as is necessary to become available for reaction with the 4-amino-3-hydrazino-5-mercapto-1,2,4-triazole, leading to observation of a false high formaldehyde level.

It is desirable to devise a test that will determine whether formaldehyde has been neutralized in an aqueous solution containing formaldehyde, where the test does not rely on a direct detection or measurement of the amount of free formaldehyde in the solution.

It is also desirable to devise a test that will enable the user to obtain a quick, reliable, and visual qualitative determination of whether formaldehyde has been neutralized in an aqueous solution containing formaldehyde.

Further, it is desirable to devise a test that is effective for use with aqueous solutions containing formaldehyde that have a pH within the substantially neutral pH range of 6.0 to 8.0 required by the EPA.

It is also desirable to devise a test that will not disturb the equilibrium between free formaldehyde and sodium bisulfte to cause the formation of free formaldehyde.

SUMMARY OF THE INVENTION

The present invention involves confirming the neutralization of formaldehyde by exposure to sulfite ions, using an indicator for detecting the presence of excess sulfite ions. The kit or test medium includes an indicator for the calorimetric determination of whether a sufficient amount of a formaldehyde neutralizer, a chemical compound which produces sulfite ions in aqueous solutions, has been added to an aqueous solution initially containing formaldehyde, wherein the solution is contacted with a test medium including a dye capable of exhibiting a color change in the presence of excess sulfite ion over formaldehyde in the solution, with the color change indicating the presence of excess sulfite ions and therefore that the formaldehyde has been substantially eliminated. The test medium may include a test strip with the dye impregnated therein or a liquid solution containing the dye.

The present invention introduces the novel approach of determining whether formaldehyde is neutralized by detecting excess formaldehyde neutralizer, rather than detecting or measuring the amount of free formaldehyde directly. An indicator dye capable of exhibiting a color change in the presence of excess formaldehyde neutralizer is used to detect whether the formaldehyde has been neutralized, where the indicator dye does not exhibit a color change when the formaldehyde neutralizer is in the presence of excess formaldehyde.

Sulfite ion, used to neutralize formaldehyde, is a reactive reducing agent. Indicator dyes or other reagents that change color upon reduction by sulfite ion at substantially neutral pH are utilized to detect the presence of excess sulfite ion. The indicator dyes exhibit a loss of color, or are "bleached" by sulfite ion at substantially neutral pH. Surprisingly, the indicator dyes were not bleached by sulfite ion in the presence of a stoichiometric excess of free formaldehyde over sulfite ion. However, when the sulfite ion level was increased to give a stoichiometric excess over the free formaldehyde present the indicator dyes were bleached. Therefore, the indicator dyes are bleached only after all of the formaldehyde has been neutralized by sulfite ion, and bleaching of the dyes provides a reliable colorimetric indication that the formaldehyde has been neutralized.

In one form thereof, a kit is provided for confirming the neutralization of formaldehyde by exposure to sulfite ions in an aqueous solution, the kit including an indicator for detecting the presence of sulfite ions.

In another form thereof, a test strip is provided for determining whether a sufficient amount of a neutralizer which produces sulfite ions in aqueous solution has been added to an aqueous solution to neutralize formaldehyde initially present in the aqueous solution, the test strip including a test medium impregnated with a dye, the dye capable of exhibiting a color change upon reaction with a stoichiometric excess of sulfite ion over formaldehyde in the aqueous solution.

In another form thereof, a method is provided of confirming the neutralization of formaldehyde by exposure to sulfite ions in an aqueous solution, where the aqueous solution is exposed to an indicator that detects the presence of sulfite ions.

In another form thereof, a method is provided of substantially neutralizing formaldehyde in an aqueous solution initially containing formaldehyde by the addition of a neutralizer that introduces ion into solution, including the steps of adding an amount of the neutralizer to the aqueous solution; providing a test strip, the test strip including a dye which is reactive with sulfite ions and exhibits a color change upon reaction with sulfite ions; contacting the test strip with the solution; inspecting the test strip for a color change; and ceasing performing the previous steps when the test strip exhibits the color change.

In another form thereof, a method is provided of confirming the neutralization of formaldehyde in aqueous solution containing formaldehyde, including the steps of providing a test strip impregnated with the dye capable of exhibiting a color change in the presence of a stoiciometric excess of sulfite ion over the amount of formaldehyde in the aqueous solution; contacting the aqueous solution with the test strip; inspecting the test strip for the color change; and if the color change is not observed, adding a compound which produces sulfite ions upon dissolution to the aqueous solution and repeating the steps until the test strip exhibits the color change.

In still another form thereof, a method is provided of substantially neutralizing formaldehyde in an aqueous solution initially containing formaldehyde by the addition of a neutralizer that produces sulfite ions in a solution, including the steps of adding an amount of the neutralizer to the solution; adding to the solution a dye having an initial color, the dye capable of exhibiting a loss of the initial odor in the presence of a stoichiometric excess of sulfite ion over the amount of formaldehyde in the solution; inspecting the solution for the color loss; and repeating the first step until the solution exhibits the color loss.

In yet another form thereof, a test kit is provided for determining neutralization of formaldehyde by exposure to sulfite ions in a solution initially containing formaldehyde, including a neutralizer that produces sulfite ions in aqueous solution; and a test strip including a dye capable of exhibiting a color change in the presence of a stoichiometric excess of sulfite ions over the amount of formaldehyde in the solution.

In order to neutralize the formaldehyde in the aqueous solution, several sulfite-containing components may be used, including alkali metal sulfites and bisulfites such as sodium sulfite, sodium bisulfite, potassium sulfite, potassium bisulfite, lithium sulfite, and lithium bisulfite, or mixtures of the foregoing compounds.

Suitable indicator dyes include dyes capable of exhibiting a color change upon reaction with a stoichiometric excess of formaldehyde; dyes having a reduction potential at neutral pH of 0.064 volt or greater; dyes capable of exhibiting the color change upon reaction with a stoichiometric excess of sulfite ion at a solution pH of from about 4.4 to about 9.4; dyes selected from indophenols, indoanilines, and indamines; and dyes selected from 2,6-dichlorophenol-indophenol and thionin. Additionally, concentrations of about 0.25 mM or less of the dye may be included within the test trip, and the test strip may be formed of a bibulous material mounted on a rigid backing material such as polystryrene.

One advantage of the present invention is that it facilitates a determination of whether formaldehyde has been neutralized by the detection of an excess amount of formaldehyde neutralizer, insuring that all of the free formaldehyde in the solution is neutralized.

Another advantage of the present invention is that the test reaction consumes only a very small amount of the excess neutralizer such that the test reaction will not upset the solution equilibrium to lead to the formation of more formaldehyde.

Another advantage of the present invention is that the test is effective within the range of 6.0 to 8.0, as specified by the EPA guidelines, but the test may also effectively test for formaldehyde neutralization within a substantially wider pH range.

Yet another advantage of the present invention is that the indicator dye may be included within a test strip which is directly contacted with the test solution, making the test easier to use.

Further, a buffer may also be included within the test strip to maintain the pH of the test reaction substantially close to neutral.

Still another advantage of the present invention is that it allows the user to make a quick and reliable visual determination of formaldehyde neutralization, thereby providing a test that is practical and easy to use.

DETAILED DESCRIPTION

The embodiments disclosed below are not intended to be exhaustive or limit the invention to the precise forms disclosed in the following detailed description and described in the following examples.

An indicator dye capable of exhibiting a color change in the presence of excess formaldehyde neutralizer is used to detect whether formaldehyde in an aqueous solution has been neutralized. The indicator dye does not exhibit a color change when the formaldehyde neutralizer is in the presence of excess formaldehyde.

Suitable indicator dyes include dyes which are capable of exhibiting a color change upon reaction with a stoichiometric excess of sulfite ion over formaldehyde in aqueous solution; dyes which have a reduction potential at neutral pH equal to or greater than 0.064 volt; dyes capable of reacting with an excess of sulfite ion over formaldehyde in a solution to exhibit the color change at a pH from about 4.4 to about 9.4; dyes which are selected from indophenols, indoanilines, and indamines; and dyes are selected from 2,6-dichlorophenol-indophenol and thionin.

Formaldehyde in aqueous solution may be neutralized by exposure to sulfite ion. Formaldehyde reacts rapidly with sulfite ion generated from a neutralizer, which herein refers to any sulfite-containing chemical component which produces sulfite ion upon dissolution in aqueous solution. For example, formaldehyde is neutralized effectively by sodium sulfite (3), sodium bisulfite (4), or a mixture thereof to yield sodium bisulfite formaldehyde, shown in the following net ionic equations:

(3) 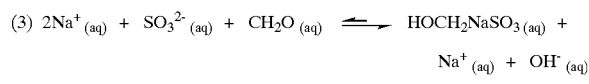

and (4) 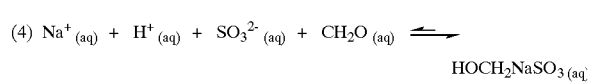

Sodium bisulfite formaldehyde is very stable in aqueous solution. However, it is not soluble in ethanol and will crystallize from aqueous solution upon the addition of ethanol to one of the following two forms containing waters of crystallization:

and

 (5)

Walker, p. 252. Sodium bisulfite formaldehyde is sufficiently stable in aqueous solution such that the equilibrium shown above in equations (3) and (4) is shifted greatly to the right, that is, toward the formation of sodium bisulfite formaldehyde and away from sodium sulfite/bisulfite and formaldehyde. In fact, the position of the equilibrium shown in equations (3) and (4) is farther to the right with formaldehyde than with other aldehydes and ketones. Noller, p. 202. Therefore, when sodium sulfite/bisulfite is added to an aqueous solution containing formaldehyde, the equilibrium concentration of sodium bisulfite formaldehyde will greatly exceed that of both sulfite ion and free formaldehyde.

In addition, other chemical compounds which produce sulfite ions upon dissolution, such as alkali metal sulfites, alkali metal bisulfites, or mixtures of alkali metal sulfites and alkali metal bisulfites, for example, may be used as formaldehyde neutralizers. This is because stable compounds analogous to sodium bisulfite formaldehyde may be formed by the reaction of other alkali metal sulfites/bisulfites with free formaldehyde. For example, potassium sulfite (6) or potassium bisulfite (7) may also be used as an effective formaldehyde neutralizer, reacting with free formaldehyde to form potassium bisulfite formaldehyde, similar to reactions (3) and (4) above, shown in the following net ionic equations:

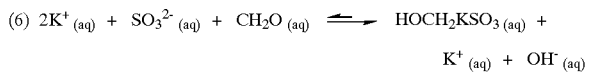

and

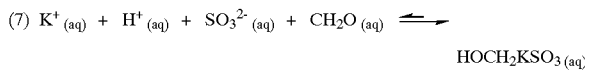

Safe neutralization of formaldehyde with sulfite ion requires a stoichiometric quantity of sulfite ion equal to that of formaldehyde, plus an excess quantity of sulfite ion to maintain the equilibrium toward sodium/potassium bisulfite formaldehyde and to keep the free formaldehyde below the 10 ppm level specified by EPA.

Sulfite ion is a reactive reducing agent that reduces certain indicator dyes such that the indicator dyes will exhibit a color change in the presence of sulfite ion. Usually, these indicator dyes either partially or totally lose their color, or are "bleached" upon reduction by sulfite ion. Surprisingly, it has been found that sulfite ion will reduce the indicator dyes in the presence of free formaldehyde in aqueous solution only very slowly and therefore the indicator dyes fail to change color for a significant time period, if at all. This is due to the fact that sulfite ion will preferably react with free formaldehyde to yield the stable sodium bisulfite formaldehyde, therefore, the concentration of sulfite ion is very low in the presence of free formaldehyde such that only a very small amount of sulfite is available to reduce the indicator dyes. However, when the concentration of sulfite ion is increased to give a stoichiometric excess over the formaldehyde present, for example, by the addition of more sodium sulfite/bisulfite to the solution the indicator dyes are reduced or "bleached" by the excess of sulfite ion to exhibit the color change.

The unexpected failure of sulfite ion to bleach the indicator dyes in the presence of formaldehyde was unpredictable before experiment. In addition, it was also unpredictable whether consumption of sulfite ion by the reduction of the indicator dyes would disturb the equilibrium, causing it to shift rapidly away from sodium bisulfite formaldehyde and toward the formation of more sulfite ion to cause bleaching of the dyes by sulfite ion released from sodium bisulfite formaldehyde. However, it has been found that sulfite ion bleaches the indicator dyes in the presence of free formaldehyde only very slowly, if at all, and in addition, that the equilibrium remains stable upon consumption of sulfite ion by the reduction of the indicator dyes.

Indicator Dyes

Indicator dyes, for the purposes of this specification, are substances which, upon reaction with sulfite ion, exhibit an observable color change. Many indicator dyes exhibit a color change upon reduction by sulfite ion at substantially neutral pH. Generally, the reduction potential of sulfite ion indicates the capacity of bisulfite/sulfite to reduce indicator dyes present in the test solution. The reduction potential for sulfite ion under acidic and basic conditions is 0.20 volt (for $H_2SO_3$) and −0.92 volt (for $Na2SO_3$), respectively. *Handbook of Chemistry and Physics,* 52nd ed., R. C. Weast, Ed., D113 (1971). At neutral pH, the solution potential of the test solution will be between 0.20 volt and −0.92 volt, and the sulfite ion present in the test solution will reduce indicator dyes with reduction potentials ($E_m^7$, at pH 7.0) higher than the solution potential. Therefore, indicator dyes with relatively higher reduction potentials will be reduced by sulfite ion more completely in the test solution.

The reduction potentials of a group of organic compounds are listed in Clark, W. M., *Oxidation-Reduction Potentials of Organic Systems,* 131–133 and 403–411 (1960). In Example II below, it is shown that the reduction potential of indigo carmine ($E_m^7$=−0.125 volt) is too low for effective reduction by sulfite ion, whereas in Example III below, it is shown that the reduction potential of thionin ($E_m^7$=0.064 volt) is adequate for effective reduction by sulfite ion. Generally, indicator dyes with reduction potentials equal to or greater than 0.064 volt may be effectively reduced by sulfite ion. These indicator dyes include indophenols, such as those listed by Clark, p. 403–405, as well as indoanilines and indamines, such as those listed by Clark, p. 407–411.

Exemplary indicator dyes include 2,6-dichlorophenol-indophenol ("DCIP") and thionin.

2,6-dichlorophenol-indophenol ("DCIP") ($E_m^7$=0.217 volt) is commercially available from Sigma Chemical Co., St. Louis, Mo. and from Aldrich Chemical Co., Milwaukee, Wis.

Thionin (also referred to as "Lauth's Violet") ($E_m^7$=0.064 volt) is commercially available from Aldrich Chemical Co., Milwaukee, Wis.

Indigo Carmine (also referred to as "Acid Blue 74") ($E_m^7$=−0.125 volt) is commercially available from Aldrich Chemical Co., Milwaukee, Wis.

The reduction of indigo carmine, DCIP, and thionin by sulfite/bisulfite in aqueous solution, respectively, is shown in the following equations, where indigo carmine, DCIP, and thionin are each bleached to exhibit a loss of color from blue to colorless upon reduction by sulfite/bisulfite:

(8) indigo carmine:

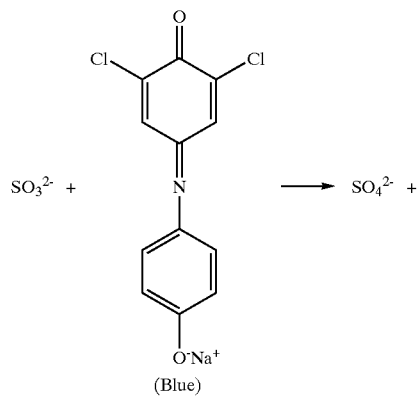

-continued

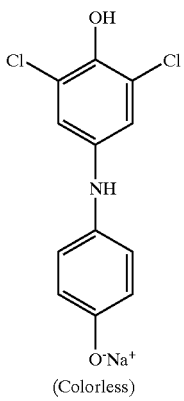
(Colorless)

(9) DCIP:

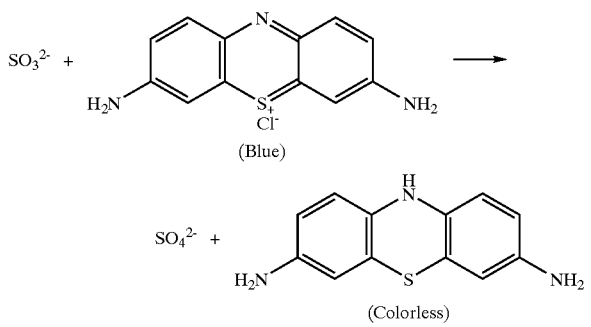

(10) thionin

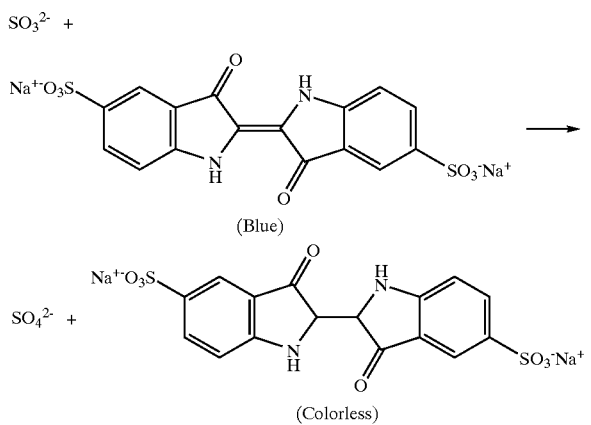

While specific examples of dyes suitable for use with the present invention have been enumerated hereinabove, such is not to be construed as limiting the invention in any manner. Rather, one of ordinary skill in the art may identify a virtually limitless number of indicator dyes related to the exemplary indicator dyes above that may be used in accordance with the present invention.

The Buffers

As described above and in the following examples, the reduction of the indicator dyes by sulfite ion is pH dependent. A buffer may be impregnated within the test strip with the indicator dye to control the pH of the test reaction when the pH of the test solution varies 5 from neutral. Buffer substances having a $pK_a$ close to 7.0 at 250° C. may be used, however, any buffer substances having a $pK_a$ in the range between about 6.0 and about 8.0 at 25° C. may also be used. Several such suitable buffer substances are listed in Perrin, D. D., Dempsey, B., *Buffers for pH and Metal Ion Control*, 156–163 (1974).

Preparation of the Test Medium

For the purposes of this specification, test medium refers to any medium or carrier in which an indicator dye may be held, which may include a test strip or a liquid solution, for example. The indicator dyes described above may be impregnated within a test strip, thereby providing a test device or test medium for the easy and rapid determination of the presence of excess sulfite ion, corresponding to the neutralization of formaldehyde. An indicator dye is first prepared in a buffer solution as described above. Then, a test strip paper, such as Schleicher & Schuell 903 paper (available from Schleicher & Schuell, Inc., Keene, N.H.) is impregnated with the indicator dye/buffer solution. A bibulous material, such as filter paper, may be used as the carrier matrix to be impregnated with the indicator dye/buffer solution.

The concentration of the indicator dye in the indicator dye/buffer solution which is impregnated into the test strip should be minimized such that the reduction of the indicator dye consumes a minimal amount of sulfite ion in the test reaction. However, the indicator dye concentration must also be great enough to provide a color change in the test strip which is unambiguous and distinctly readable for most users of the test strips. In Example IV, concentrations of 0.25 mM and 0.08 mM of DCIP and Thionin, respectively, were found to be effective to produce a distinctly readable color change upon reduction by sulfite ion while consuming only a nominal amount of sulfite ion. However, it should be understood that lesser concentrations of indicator dyes may be used in test strips to obtain test strips which are functional in accordance with the present invention.

The impregnated test strip is then dried in a manner that does not adversely affect the solution impregnated within the test strip. A forced air oven may be used to dry the test strip, such as a Model 18 forced air oven manufactured by Precision Scientific of Winchester, Va. The test strip may be dried, for example, at a temperature from 120° to 200° F. for 3 to 30 minutes, where the drying time is dependent upon the temperature and the amount of air circulation around the test strip. If drying temperatures lower than 120° F. are used, drying times longer than 30 minutes are typically required. After drying, the test strips may then be fabricated into test pads. The test pads are mounted onto and secured to a rigid backing material, such as polystyrene, by any suitable means, such as with a double sided tape (415 polyester tape, supplied by 3M Company, St. Paul, Minn.).

Alternatively, an indicator may be used to confirm the neutralization of formaldehyde in aqueous solution without using a test strip, as demonstrated below in Example V, where the test medium may include a liquid solution of the dye. First, a neutralizer such as sodium sulfite/bisulfite is added to the solution to neutralize the formaldehyde, and the pH of the solution is adjusted to the neutral range, if necessary. Alternatively, a buffer may be added to the solution before the addition of the neutralizer to maintain the pH in a desired range, such as the buffers described above. Then, a small amount of a solution of an indicator dye is added to the solution. Generally, the indicator dye will change the color of the solution according to the color of the indicator dye, and, if the solution remains colored, the dye has not been reduced by an excess amount of sulfite ion, indicating that the formaldehyde has not been neutralized. If the solution remains colorless after the addition of the indicator dye or becomes colorless after a certain elapsed time, the dye has been reduced by an excess amount of sulfite ion, indicating neutralization of the formaldehyde in the solution. The necessary elapsed time by which the solution must change color to correctly indicate neutralization of the formaldehyde must be empirically determined for each particular dye. Generally, this method is more useful for formaldehyde-containing solutions with a relatively small total volume.

Contacting the Test Device with the Test Solution and Examining the Test Medium

In use, the free end of the polystryrene backing serves as a handle for the user. The test strip is held by the handle, and the test pad end is then dipped into the test solution and quickly removed. Alternatively, an aliquot of liquid from the test solution may be removed in a suitable manner and applied to the test strip by pipette, spatula, or swab.

The test strip may be inspected or read for a visual color change by the user after an elapsed time following removal of the test strip from the test solution. This elapsed time or "reaction time" is a function of the particular indicator dye used. There is usually no need for instrumentation to aid in the inspection. The user may simply note a color change or loss of color, such as those described in the Examples below, to indicate whether formaldehyde has been neutralized in the test solution. Generally, a test strip impregnated with DCIP will turn from blue to white, with the blue color indicating that the none of the DCIP was reduced by sulfite ion and the white color indicating that all of the DCIP was reduced by sulfite ion. Therefore, with respect to tests strips impregnated with DCIP, blue indicates incomplete neutralization of formaldehyde, and white indicates complete neutralization of formaldehyde. A test strip impregnated with thionin will gradually turn from blue to light blue to gray, with the blue color indicating that the thionin was not reduced by sulfite ion, and the gray color indicating that substantially all of the thionin was reduced by sulfite ion. Generally, light blue also indicates that substantially all of the thionin was reduced, depending upon the elapsed reaction time, as shown below in Examples IV and V. Therefore, with respect to test strips impregnated with thionin, blue indicates incomplete neutralization of formaldehyde, light blue may indicate complete neutralization of formaldehyde, and gray indicates complete neutralization of formaldehyde. If the test strip indicates incomplete neutralization following contact with the solution, more neutralizer may then be added to the solution, followed by contacting a second test strip with the solution and observing the color of the second test strip. This process may be repeated until a test strip indicates that the formaldehyde in the solution is neutralized.

Reference color blocks may be provided to aid a user in determining when a color change or loss of color has occurred. For example, a light blue reference color block may be provided with the thionin test strips to show the specific light blue color which indicates complete neutralization of formaldehyde, in order to eliminate ambiguity caused by the varying color interpretations of different users.

EXAMPLES 2,6-dichlorophenol-indophenol ("DCIP") indicator dye was obtained from Sigma Chemical Co., St. Louis, Mo. Thionin and indigo carmine indicator dyes were obtained from Aldrich Chemical Co., Milwaukee, Wis.

Schleicher & Scheull 903 test strip paper was obtained from Schleicher & Scheull, Inc., Keene, N.H. Double sided tape, 415 polyester tape, was obtained from 3M Company, St. Paul, Minn.

The following abbreviations are used in the Examples:

TABLE I

| Abbreviations | |
|---|---|
| Abbreviation | Full Word |
| A | absorbance |
| ° C. | degrees centigrade |
| g | gram |
| M | molar |
| mM | millimolar |
| µL | microliter |
| nm | nanometer |
| min | minutes |

Percentages used indicate weight in grams of substance per 100 grams of aqueous solution (% w/w), unless otherwise indicated.

Example I

Comparison of a Prior Known Test Method with an Exemplary Test Method

Several standard formaldehyde solutions were neutralized or partially neutralized with the sodium sulfite/sodium bisulfite neutralizer (NEUTRALEX™) supplied in the Tissue-Tek® test kit. These solutions were then tested with the Tissue-Tek® test strips (impregnated with 4-amino-3-hydrazino-5-mercapto-1,2,4-triazole or a variant thereof) and with exemplary test strips impregnated with DCIP or thionin.

The Tissue-Tek® assay procedure involves the steps of: (1) measuring 5 mL of sample solution into a specially marked container supplied with the Tissue-Tek® kit; (2) adding 20 drops of 5 N sodium hydroxide; (3) dipping a test strip into the mixture prepared in steps (1) and (2) for one second; and (4) one minute later, reading the test strip color by comparison to a color chart provided with the test kit, which includes color blocks corresponding 0, 10, 20, 40, 60 and 100 ppm formaldehyde. As an initial quality control, standards containing 0, 10 and 100 ppm formaldehyde in water were tested, and the observed test strip readings are presented in Table II below:

TABLE II

| Prior Known Test Method Control Results | |
|---|---|
| Formaldehyde Concentration | Test Strip Reading |
| 0 ppm | 0 ppm |
| 10 ppm | 10 to 20 ppm |
| 100 ppm | 100 ppm |

The test strip tested with the 10 ppm standard read slightly above 10 ppm; otherwise, the test functioned essentially as expected.

Next, several standard solutions with known formaldehyde concentrations were neutralized or partially neutralized with the sodium sulfite/sodium bisulfite neutralizer (NEUTRALEX™) supplied with the Tissue-Tek® test kit, which is a white powder. The amount of NEUTRALEX™ recommended by the Tissue-Tek® test kit for the neutralization of formaldehyde is 700 g NEUTRALEX™ per gallon of 4.0% formaldehyde. Information on the relative proportions of sodium bisulfite and sodium sulfite in the NEUTRALEX™ powder was unavailable.

Completely and partially neutralized formaldehyde solutions for testing were prepared from 10% phosphate buffered formalin purchased from Fisher Scientific, Itasca, Ill. and found to contain 4.02% (w/w) formaldehyde. Fifty gram portions of the 10% formalin were neutralized with 100, 90, 80 and 70% of the recommended level of NEUTRALEX™. These solutions were tested with the Tissue-Tek® NEUTRALEX™ Aldehyde Test Kit and with exemplary DCIP and thionin test strips, prepared as described in Example IV below. The DCIP and thionin test strips were read at 15 seconds and 15 minutes, respectively, and the following results were observed:

TABLE III

Prior Known Test Method and Exemplary Test Method Results with Formaldehyde Neutralized with Various Amounts of Commercial Neutralizer

| NEUTRALEX ™ Percent of Recommended Level | NEUTRALEX ™ Aldehyde Test Kit Strip Reading | Exemplary Test Strip Readings[1] | |
|---|---|---|---|
| | | DCIP[2] | Thionin[3] |
| 100 | 0–10 ppm | White | Gray |
| 90 | 0–10 ppm | White | Gray |
| 80 | 0–10 ppm | Blue | Blue |
| 70 | 0–10 ppm | Blue | Blue |

[1] White and gray = complete neutralization; Blue = incomplete neutralization
[2] Readings at 15 seconds.
[3] Readings at 15 minutes.

The 70% neutralized solution contained approximately 1.37 M formaldehyde. Assuming the NEUTRALEX™ neutralizer was 100% sodium bisulfite (which provides the highest possible capacity for neutralization because the molecular weight of sodium bisulfite is less than that of sodium sulfite), the 70% solution would be about 1.23 M bisulfite and 0.14 M free formaldehyde (4200 ppm), and therefore should have given a test strip reading of at least 100 ppm formaldehyde. Instead, as indicated in Table III above, the observed reading was 10 ppm. The DCIP and thionin test strips each indicated an incomplete neutralization when tested with the solutions treated with 70 and 80% of the recommended levels of NEUTRALEX™.

An additional experiment was conducted with a 3.93% formaldehyde solution to which sodium sulfite was added, where the stoichiometry of the neutralization reaction could be calculated more accurately due to the fact that the composition of the sodium sulfite is known. Aliquots of the 3.93% formaldehyde solution were treated with 0.9, 0.95 and 1.0 moles of sodium sulfite per mole of formaldehyde, and the resulting alkaline solutions were then adjusted to neutral pH with hydrochloric acid. The three solutions were tested with the Tissue-Tek® NEUTRALEX™ Aldehyde Test Kit and with the exemplary DCIP test strips, and the following results were observed:

TABLE IV

Readings Obtained with a Prior Known Test Method and the Exemplary Test Method on Formaldehyde Solutions Neutralized with Various Amounts of Sodium Sulfite

| Sodium Sulfite (mole/mole formaldehyde) | Tissue-Tek ® NEUTRALEX ™ Test Strip reading | Exemplary DCIP Test Strip reading |
|---|---|---|
| 1.0 | 20 ppm | Neutralization incomplete |
| 0.95 | 10–20 ppm | Neutralization incomplete |
| 0.9 | 20 ppm | Neutralization incomplete |

As indicated in Table IV, the Tissue-Tek® test strip readings were 10 to 20 ppm formaldehyde, while the exemplary DCIP test strips indicated incomplete neutralization for all three of the sodium sulfite/formaldehyde solutions. Stoichiometric calculations showed that the solution prepared with 0.9 mole sodium sulfite/mole formaldehyde contained approximately 4200 ppm free formaldehyde, which the Tissue-Tek® test strips failed to detect.

Example II

Evaluation of Indigo Carmine Test Strips

1. Preparation of Indigo Carmine Test Strips

Fifty milliliters (50.0 mL) of 0.5 M sodium citrate buffer, pH 6.0, was combined with 0.5 mL of 10 mM indigo carmine (purchased from Sigma Chemical Co., St. Louis, Mo.) in water. The mixture was impregnated into Schleicher & Schuell 903 paper (Schleicher & Schuell, Keene, N.H.) and dried at 60° C. in a forced air oven (Precision Scientific, Model 18). Double sided tape (415 polyester tape) purchased from 3M, St. Paul, Minn. was applied to one side of the dry paper. The paper was then fabricated into 0.2 inch square test pads mounted on one end of 0.2 inch wide strips of polystyrene.

2. Tests with Indigo Carmine Test Strips

The formaldehyde solutions neutralized in Example I with various levels of NEUTRALEX™ were also tested with indigo carmine test strips. The test strips were read 15 minutes after dipping them into the test solutions. The blue color of the test strips did not exhibit observable bleaching after contact with any of the neutralized solutions. The reduction potential of indigo carmine ($E_m^7 = -0.125$ volt) is too low for indigo carmine to be used as an effective indicator dye in a test for excess sulfite ion.

Example III

Studies with Thionin and DCIP

1. Reduction of Thionin by Bisulfite/Sulfite at Various pH

The rates of reduction of thionin by sulfite/bisulfite in an aqueous solution were determined by measuring the rates of decrease in absorbance at 599 nm with a Shimadzu UV160U spectrophotometer (Shimadzu Corporation, Kyoto, Japan) at room temperature. Reactions were carried out with the following buffers: 0.1 M Tris-phosphate, pH 8.5; 0.1 M Tris-HCl, pH 8.0; 0.1 M sodium phosphate, pH 7.0; and 0.1 M sodium citrate buffers at pH 6.0, 5.0 and pH 4.0.

The following solutions were prepared, and the rates of reduction (bleaching) of the blue color of thionin determined by measuring the absorbance with the spectrophotometer (Shimadzu UV160U) immediately after mixing with sodium sulfite:

TABLE V

Reduction of Thionin by Sulfite/Bisulfite at Various pH

| pH | Buffer($\mu$L) | 2.0 mM Thionin ($\mu$L) | 250 mM Sodium sulfite ($\mu$L) | A 599 nm/min. |
|---|---|---|---|---|
| 8.0 | 750 | 50 | 200 | −0.133 |
| 7.0 | 750 | 50 | 200 | −0.273 |
| 6.0 | 750 | 50 | 200 | −0.102 |
| 5.0 | 750 | 50 | 200 | −0.005 |
| 4.0 | 750 | 50 | 200 | 0.000 |

The data above show that the reaction rate of thionin with sulfite/bisulfite is dependent on the solution pH, where the reaction proceeds most rapidly at pH 7.0.

2. Reduction of DCIP by Sulfite/Bisulfite at Various pH

DCIP is a phenolic dye with a red color at acidic pH. The phenolate ion of DCIP is blue in color, and ionizes with a $pK_a$=5.7. The rates of reduction (bleaching) of the phenolate ion at various pH were determined by measuring the absorbance at room temperature with the spectrophotometer (Shimadzu UV160U) immediately after mixing DCIP in the buffers listed above with sodium sulfite:

TABLE VII

Reduction of DCIP by Sulfite/Bisulfite at Various pH

| pH | Buffer Volume ($\mu$L) | 1.0 mM DCIP ($\mu$L) | 1.0 mM Sodium Sulfite ($\mu$L) | A 600 nm/min |
|---|---|---|---|---|
| 8.5 | 850 | 100 | 50 | −0.044 |
| 8.0 | 850 | 100 | 50 | −0.051 |
| 7.0 | 850 | 100 | 50 | −0.172 |
| 6.0 | 850 | 100 | 50 | −0.162 |
| 5.0 | 850 | 100 | 50 | −0.058 |
| 4.0 | 850 | 100 | 50 | −0.027 |

As indicated above, the reaction rate of DCIP with sulfite/bisulfite is dependent on the solution pH, where DCIP is readily reduced between pH 6 and pH 7.

Example VI

Studies with DCIP and Thionin Test Strips

1. Preparation of DCIP Test Strips

DCIP was purchased as the sodium salt from Sigma Chemical Co., St. Louis, Mo. A 0.25 mM solution was prepared in a 0.5 M sodium phosphate buffer, pH 7.0. Schleicher & Schuell 903 paper was purchased from Schleicher & Schuell, Inc., Keene, N.H., and was impregnated with the DCIP/buffer solution and then dried at 60° C. in a forced air oven (Precision Scientific, Model 18). Double sided tape (415 polyester tape) purchased from 3M, St. Paul, Minn. was applied to one side of the dry paper. The paper was then fabricated into 0.2 inch square test pads mounted on one end of 0.2 inch wide strips of polystyrene.

2. Preparation of Thionin Test Strips

A two-dip process was used to prepare thionin test strips. The first impregnation solution comprised a 0.5 M sodium phosphate buffer, pH 7.0. Schleicher & Schuell 903 paper was impregnated with the 0.5 M sodium phosphate buffer and dried at 60° C. in a forced air oven (Precision Scientific, Model 18).

The second impregnation solution was prepared by combining 2.0 mL of 2.0 mM thionin (purchased from Aldrich Chemical Co., Milwaukee, Wis.) in water with 48 mL ethanol, resulting in a 0.08 mM thionin solution. The dry paper with the impregnated buffer was dipped into this solution and then dried again at 60° C. in a forced air oven. The paper was assembled into test strips as described above.

3. Effects of Reaction Time on Results Obtained with DCIP and Thionin Test Strips Standard formaldehyde solutions were prepared and tested with test strips impregnated with DCIP or thionin in order to determine the amount of elapsed time required for the test strips to exhibit a change in color.

An aqueous solution of formaldehyde was prepared, and found by sodium sulfite titration to contain a formaldehyde concentration of 3.93%. Aliquots of this solution were neutralized or partially neutralized with sodium sulfite as in Example I, and were tested with DCIP and thionin test strips. Test strip readings were recorded at the indicated times after the test strips were dipped into the solutions and immediately removed. The following results were observed:

TABLE VII

DCIP and Thionin Test Strip Colors as a Function of Reaction Time and Ratio of Sulfite/Bisulfite to Formaldehyde

| Sulfite/Formaldehyde | DCIP Test Strip Readings Reaction Time (min) | | | | |
|---|---|---|---|---|---|
| (mole/mole) | 0.25 | 0.5 | 1.0 | 2.0 | 5.0 |
| 0.95 | Blue | Blue | Blue | Blue | Blue |
| 1.0 | Blue | Blue | Blue | Blue | Blue |
| 1.05 | White | White | White | White | White |

| Sulfite/Formaldehyde | Thionin Test Strip Readings Reaction Time (min) | | | | | |
|---|---|---|---|---|---|---|
| (mole/mole) | 0.5 | 1.0 | 2.0 | 5.0 | 10 | 15 |
| 0.95 | Blue | Blue | Blue | Blue | Blue | Blue |
| 1.0 | Blue | Blue | Blue | Blue | Blue | Blue |
| 1.05 | Blue | Blue | Blue | Blue | Light Blue | Gray |
| 1.1 | Blue | Blue | Blue | Light Blue | Gray | Gray |

Each data point represents three replicate test strip readings.

Blue=incomplete neutralization. White and gray=complete neutralization.

As indicated above, the thionin test strips were bleached at a slower rate than the DCIP test strips, and therefore, appropriate read times should be determined empirically for different indicator dye systems.

Both the DCIP and thionin test strips exhibited no color change after contact with solutions having no excess sulfite ion present. Test strips impregnated with DCIP exhibited a blue-to-white color change within 15 seconds after contact with solutions containing an excess of sulfite ion over formaldehyde. Test strips impregnated with thionin exhibited a color change from blue to light blue to gray, requiring about 15 minutes for the color change to fully develop. The color change observed with thionin occurred more rapidly as the excess of sulfite ion over formaldehyde was increased in the test solutions, therefore, less than 15 minutes were required for the color change to fully develop in the test solutions having increasing excesses of sulfite ion present.

In an additional experiment, aliquots of 10% formalin containing 4.02% formaldehyde, as determined by sodium sulfite titration, were neutralized with potassium sulfite to give 0.94 or 1.04 mole sulfite/mole formaldehyde. These solutions were tested with DCIP and thionin test strips and the colors were observed as a function of time. The following results were observed:

TABLE VIII

DCIP and Thionin Test Strip Colors as a Function of Reaction Time and Extent of Neutralization with Potassium Sulfite

|  | DCIP Test Strip Readings | | | | |
|---|---|---|---|---|---|
| Sulfite/Formaldehyde | 0.25 | 0.5 | 1.0 | 2.0 | 5.0 |
| 0.94 | Blue | Blue | Blue | Blue | Blue |
| 1.04 | White | White | White | White | White |

| Sulfite/Formaldehyde | Thionin Test Strip Readings Reaction Time (min) | | | | | |
|---|---|---|---|---|---|---|
| (mole/mole) | 0.5 | 1.0 | 2.0 | 5.0 | 10 | 15 |
| 0.94 | Blue | Blue | Blue | Blue | Blue | Blue |
| 1.04 | Blue | Blue | Blue | Blue | Light Blue | Gray |

Each data point represents three replicate test strip readings.

Blue=incomplete neutralization. White and gray=complete neutralization.

As shown in Table VIII, the test strips tested with potassium sulfite/formaldehyde gave readings similar to those tested with sodium sulfite/formaldehyde (Table VII).

4. Tests with DCIP and Thionin Test Strips at Varying Ratios of Sulfite/Bisulfite to Formaldehyde Standard formaldehyde solutions containing sulfite ion present in various amounts slightly less than, slightly more than, and equivalent to the amount of formaldehyde in the solutions were tested with test strips impregnated with either DCIP or thionin. These tests were performed in order to determine whether consumption of the sulfite ion by the indicator dyes would disturb the formaldehyde/sodium bisulfite formaldehyde equilibrium in solutions having ratios of sulfite ion and formaldehyde which are nearly equivalent. Neutralization of the formaldehyde in the solution requires sulfite ion to be present in a 1:1 mole ratio with formaldehyde, and also a very slight excess of sulfite ion to maintain the formaldehyde/sodium bisulfite formaldehyde equilibrium toward sodium bisulfite formaldehyde.

An aqueous solution of formaldehyde was prepared, and found by sodium sulfite titration to contain a concentration of formaldehyde of 3.93%. Aliquots of this solution were neutralized or partially neutralized with sodium sulfite such that sulfite ion was present in amounts ranging from 0.9 to 1.3 mole of sodium sulfite per mole of formaldehyde. The solutions were adjusted to a pH of between 6.0 to 8.0 with hydrochloric acid. The solutions were then tested with the DCIP and thionin test strips, using read times of 15 seconds and 15 minutes, respectively. The following results were observed:

TABLE IX

DCIP and Thionin Test Strip Readings at Varying Ratios of Sulfite/Bisulfite to Formaldehyde

| Sodium Sulfite | Test Strip Readings | |
|---|---|---|
| (mole/mole) | DCIP Test Strips | Thionin Test Strips |
| 0.9 | Blue | Blue |
| 0.95 | Blue | Blue |
| 1.0 | Blue | Blue |
| 1.05 | White | Gray |
| 1.1 | White | Gray |
| 1.3 | White | Gray |

Each data point represents three replicate test strip readings.

Blue=incomplete neutralization. White and gray=complete neutralization.

The test strip readings were consistent with the expected results, given the ratios of sulfite to formaldehyde used to prepare the test solutions. Specifically, in the solutions where sulfite ion was present in 0.9 and 0.95 mole ratios to formaldehyde, both the DCIP and thionin test strips correctly indicated that neutralization was incomplete. Also, in the solutions where sulfite ion was present in 1.05, 1.1 and 1.3 mole ratios to formaldehyde, both the DCIP and thionin test strips correctly indicated that neutralization was complete. When the solution contained a 1:1 ratio of sulfite ion to formaldehyde, both the DCIP and thionin test strips indicated that neutralization was incomplete, because all of the sulfite ion reacted with the formaldehyde and there was no excess sulfite ion in the solution to reduce the DCIP and thionin indicator dyes. The amounts of DCIP and thionin indicator dyes in the test strips (0.25 mM and 0.08 mM, respectively) were very low in comparison to the levels of sodium sulfite (0.9 mole or higher) added to the test solutions such that the DCIP and thionin indicator dyes did not consume a significant portion of the sulfite ion in the test solutions in order to produce the above results.

5. Effects of Test Solution pH on DCIP and Thionin Test Strip Readings

To determine the effectiveness of test strips impregnated with thionin and DCIP at varying test solution pH, aqueous standard solutions of formaldehyde were prepared and sodium sulfite was added to the solutions such that sulfite ion was present in either 0.9 or 1.1 molar equivalents to the amount of formaldehyde present in the solutions. When sulfite ion is present in a 0.9 molar equivalent to formaldehyde, the formaldehyde in the solution is only partially neutralized. In other words, a quantity of free formaldehyde remains present in the test solution. When sulfite ion is present in a 1.1 molar equivalent to formaldehyde, the formaldehyde in the solution is completely neutralized, and no free formaldehyde is present in the solution.

These partially neutralized/neutralized solutions were at a high pH due to the reaction of sulfite ion with the formaldehyde, which results in an alkaline solution. The pH of these solutions was adjusted with hydrochloric acid to various levels, and the solutions were then tested with the DCIP and thionin test strips. The DCIP test strips and the thionin test strips were read 15 seconds and 15 minutes, respectively, after they were dipped into the various test solutions and then immediately removed. The following results were observed:

TABLE X

DCIP and Thionin Test Strip Readings at Varying pH

| Test Solution | 0.9 equivalent Na$_2$SO$_3$ | | 1.1 equivalent Na$_2$SO$_3$ | |
| --- | --- | --- | --- | --- |
| pH | DCIP | Thionin | DCIP | Thionin |
| 10.4 | Blue | Blue | Blue | Blue |
| 9.4 | Blue | Blue | White | Gray |
| 7.7 | Blue | Blue | White | Gray |
| 6.9 | Blue | Blue | White | Gray |
| 5.2 | Blue | Blue | White | Gray |
| 4.4 | Blue | Blue | White | Gray |

Each data point represents three replicate test strip readings.

Blue=incomplete neutralization. White and gray=complete neutralization.

As indicated above, both the DCIP and thionin test strips produced correct readings as tested with solutions in the range of from pH 4.4 to pH 9.4. The buffering capacity of the test strips was inadequate to correct for the solutions at pH 10.4, thereby resulting in the observed incorrect readings at pH 10.4. However, incorrect results such as that observed at pH 10.4 will not result in an incorrect reading if the pH of the neutralized formaldehyde solution is first adjusted to the neutral range.

Example V

Studies with DCIP and Thionin in Solution for Testing Partially and Completely Neutralized Formaldehyde Solutions of indicator dyes may be added to formaldehyde solutions after the addition of sulfite/bisulfite to test for neutralization of the formaldehyde. Aliquots of formalin, containing 4.06% w/w formaldehyde, were neutralized with 0.95 or 1.05 mole sodium sulfite/mole formaldehyde, and the solutions were then adjusted to pH 6.8 with concentrated hydrochloric acid. One milliliter aliquots of the solutions were combined with one drop of 2.0 mM DCIP or 2.0 mM thionin (each dissolved in water) and the colors were observed over time. The following results were observed:

TABLE XI

Colors of Partially and Completely Neutralized Formaldehyde Solutions Containing DCIP or Thionin

| | DCIP | | Thionin | |
| --- | --- | --- | --- | --- |
| Read | 0.9 | 1.05 | | |
| Time (min) | mole/mole | mole/mole | 0.95 mole/mole | 1.05 mole/mole |
| 0.2 | Blue | Colorless | Blue | Blue |
| 1.0 | Blue | Colorless | Blue | Light blue |
| 2.0 | Blue | Colorless | Blue | Light blue |
| 5.0 | Blue | Colorless | Blue | Light blue |
| 10 | Light blue | Colorless | Blue | Light blue |
| 30 | Colorless | Colorless | Blue | Colorless |
| 60 | Colorless | Colorless | Blue | Colorless |

The solution containing DCIP neutralized with 1.05 mole sodium sulfite/mole formaldehyde became colorless by 0.2 minute, while the solution partially neutralized with 0.95 mole sodium sulfite/mole formaldehyde still had some blue color at 10 minutes. Therefore, DCIP may be added to sulfite/formaldehyde solutions to test for complete neutralization using reaction times of 0.2 to 10 minutes to observe the color. The DCIP was bleached very slowly in the partially neutralized solution by trace amounts of free sulfite ion made available by the reversal of the formaldehyde/sodium bisulfite formaldehyde equilibrium.

Thionin added to completely neutralized formaldehyde was bleached relatively slowly, and a read time of 30 minutes was required to distinguish between partially and completely neutralized formaldehyde.

Similar studies were conducted with formaldehyde neutralized with potassium sulfite. Aliquots of formalin were neutralized with potassium sulfite to give 0.94 or 1.04 mole sulfite/mole formaldehyde solutions. The solutions were then adjusted to neutral pH with concentrated hydrochloric acid. One milliliter aliquots were mixed with DCIP or thionin, as described above, and the colors were observed. The following results were observed:

TABLE XII

Colors of Solutions Containing DCIP or Thionin and Formaldehyde Partially or Completely Neutralized by Potassium Sulfite

| | DCIP | | Thionin | |
| --- | --- | --- | --- | --- |
| Read | 0.94 | 1.04 | | |
| Time (min) | mole/mole | mole/mole | 0.94 mole/mole | 1.04 mole/mole |
| 0.2 | Blue | Colorless | Blue | Blue |
| 1.0 | Blue | Colorless | Blue | Blue |
| 2.0 | Blue | Colorless | Blue | Blue |
| 10 | Light blue | Colorless | Blue | Light blue |
| 15 | Light blue | Colorless | Blue | Light blue |
| 30 | Light blue | Colorless | Blue | Colorless |
| 60 | Light blue | Colorless | Blue | Colorless |

As indicated above, neutralization with potassium sulfite produced similar data as neutralization with sodium sulfite (Table XI) when DCIP or thionin were present in the solution, and therefore the extent of neutralization of formaldehyde with potassium sulfite may be determined with DCIP and thionin by the same methods demonstrated for neutralization with sodium sulfite.

Although several broad examples which incorporate the present invention have been described above, it is to be understood that the present invention is not to be limited by the examples disclosed herein. Indeed, the disclosure and examples above teach one of ordinary skill a virtually limitless number of conditions which would be within the scope of the claims appended hereto.

Further, while this invention has been described as having a preferred design, the present invention may be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A kit for confirming the neutralization of formaldehyde by exposure to sulfite ions in an aqueous solution, said kit comprising an indicator for detecting the presence of sulfite ions.

2. The kit of claim 1, wherein said indicator is a dye capable of exhibiting a color change upon reaction with a stoichiometric excess of sulfite ion over formaldehyde in the aqueous solution.

3. The kit of claim 2, wherein said dye has a reduction potential at neutral pH of 0.064 volt or greater.

4. The kit of claim 2, wherein said dye is capable of reacting with said stoichiometric excess of sulfite ion at a pH of said aqueous solution from about 4.4 to about 9.4.

5. The kit of claim 3, wherein said dye is selected from indophenols, indoanilines, and indamines.

6. The kit of claim 5, wherein said dye is selected from the group consisting of 2,6-dichlorophenol-indophenol and thionin.

7. The kit of claim 1, wherein said kit further comprises a test medium containing said dye.

8. The kit of claim 7, wherein said test medium is a solution containing said dye.

9. The kit of claim 7, wherein said test medium is a test strip, said dye impregnated within said test strip.

10. The kit of claim 1, wherein a neutralizer which produces sulfite ions in aqueous solution is added to the aqueous solution to produce the sulfite ions, said neutralizer selected from alkali metal sulfites, alkali metal bisulfites, and a mixture of alkali metal sulfites and alkali metal bisulfites.

11. A test strip for determining whether a sufficient amount of a neutralizer which produces sulfite ions in aqueous solution has been added to an aqueous solution to neutralize formaldehyde initially present in the aqueous solution, said test strip comprising:

a test medium impregnated with a dye, said dye capable of exhibiting a color change upon reaction with a stoichiometric excess of sulfite ion over formaldehyde in the aqueous solution.

12. The kit of claim 11, wherein said dye has a reduction potential at neutral pH of 0.064 volt or greater.

13. The kit of claim 11, wherein said dye is capable of reacting with said stoichiometric excess of sulfite ion at a solution pH of from about 4.4 to about 9.4.

14. The test strip of claim 12, wherein said dye is selected from indophenols, indoanilines, and indamines.

15. The test strip of claim 14, wherein said dye is selected from the group consisting of 2,6-dichlorophenol-indophenol and thionin.

16. The test strip of claim 11, wherein said dye is prepared in a buffer solution with the concentration of said dye in said buffer solution about 0.25 mM or less, said buffer solution impregnated within said test strip.

17. The test strip of claim 16, wherein said buffer solution is capable of maintaining a pH of from about 6.0 to about 8.0.

18. The test strip of claim 11, wherein said neutralizer is selected from alkali metal sulfites, alkali metal bisulfites, and a mixture of alkali metal sulfites and alkali metal bisulfites.

19. The test strip of claim 11, wherein said test strip is comprised of a bibulous material mounted upon a rigid backing material.

20. A method of confirming the neutralization of formaldehyde by exposure to sulfite ions in an aqueous solution, the method comprising exposing the aqueous solution to an indicator that detects the presence of sulfite ions.

21. The method of claim 20, wherein said indicator is a dye capable of exhibiting a color change upon reaction with a stoichiometric excess of sulfite ion over formaldehyde in the aqueous solution.

22. The method of claim 21, wherein said dye is impregnated within a test strip.

23. The method of claim 21, wherein said dye has a reduction potential at neutral pH of 0.064 volt or greater.

24. The method of claim 21, wherein said dye is capable of reacting with said sulfite ions at a pH of said aqueous solution of from about 4.4 to about 9.4.

25. The method of claim 23, wherein said dye is selected from indophenols, indoanilines, and indamines.

26. The method of claim 25, wherein said dye is selected from the group consisting of 2,6-dichlorophenol-indophenol and thionin.

27. The method of claim 20, wherein a neutralizer that produces sulfite ions in aqueous solution is added to the aqueous solution to produce said sulfite ions, said neutralizer selected from alkali metal sulfites, alkali metal bisulfites, and a mixture of alkali metal sulfites and alkali metal bisulfites.

28. A method of substantially neutralizing formaldehyde in an aqueous solution initially containing formaldehyde by the addition of a neutralizer that produces sulfite ions in the solution, the method comprising the steps of:

(a) adding an amount of the neutralizer to the aqueous solution;

(b) providing a test strip, the test strip including a dye which is reactive with sulfite ions and exhibits a color change upon reaction with sulfite ions;

(c) contacting the test strip with the solution;

(d) inspecting the test strip for a color change; and (e) ceasing performing steps (a) through (d) when the test strip exhibits the color change.

29. The method of claim 28, wherein said dye has a reduction potential at neutral pH of 0.064 volt or greater.

30. The method of claim 28, wherein said dye is capable of reacting with the sulfite ions at a pH of the aqueous solution of from about 4.4 to about 9.4.

31. The method of claim 29, wherein said dye is selected from indophenols, indoanilines, and indamines.

32. The method of claim 31, wherein the dye is selected from the group consisting of 2,6-dichlorophenol-indophenol and thionin.

33. The method of claim 28, wherein the neutralizer is selected from alkali metal sulfites, alkali metal bisulfites, and a mixture of alkali metal sulfites and alkali metal bisulfites.

34. The method of claim 28, wherein the test strip further includes a buffer impregnated therein, said buffer capable of maintaining a pH of from about 6.0 to about 8.0.

35. A method of confirming the neutralization of formaldehyde in an aqueous solution containing formaldehyde, the method comprising the steps of:

(a) providing a test strip impregnated with a dye capable of exhibiting a color change in the presence of a stoichiometric excess of sulfite ion over the amount of formaldehyde in the aqueous solution;

(b) contacting the aqueous solution with the test strip;

(c) inspecting the test strip for the color change; and (d) if the color change is not observed, adding to the solution a compound which produces sulfite ions upon dissolution, and repeating steps (a) through (d) until the test strip exhibits the color change.

36. The method of claim 35, wherein said dye has a reduction potential at neutral pH of 0.064 volt of greater.

37. The method of claim 35, wherein said dye is capable of reacting with the sulfite ions at a pH of the aqueous solution of from about 4.4 to about 9.4.

38. The method of claim 36, wherein said dye is selected from indophenols, indoanilines, and indamines.

39. The method of claim 38, wherein the dye is selected from the group consisting of 2,6-dichlorophenol-indophenol and thionin.

40. The method of claim 35, wherein the test strip is comprised of a bibulous carrier material mounted upon a rigid backing material.

41. The method of claim 35, wherein the neutralizer is selected from alkali metal sulfites, alkali metal bisulfites, and a mixture of alkali metal sulfites and alkali metal bisulfites.

42. The method of claim 35, wherein the test strip further includes a buffer impregnated therein, the buffer capable of providing a pH in the range of from about 6.0 to about 8.0.

43. A method of substantially neutralizing formaldehyde in an aqueous solution initially containing formaldehyde by the addition of a neutralizer that produces sulfite ions in the solution, the method comprising the steps of:

(a) adding an amount of the neutralizer to the solution;
  (b) adding to the solution a dye having an initial color, the dye capable of exhibiting a loss of the initial color in the presence of a stoichiometric excess of sulfite ion over the amount of formaldehyde in the solution;
  (c) inspecting the solution for the color loss; and
  (d) repeating step (a) until the solution exhibits the color loss.

44. The method of claim 43, wherein the method further includes the additional step of adding a buffer to the aqueous solution before the addition of the neutralizer, said buffer capable of providing a pH of from about 6.0 to about 8.0.

45. The method of claim 43, wherein said dye has a reduction potential at neutral pH of 0.064 volt or greater.

46. The method of claim 43, wherein said dye is capable of exhibiting the color loss at a solution pH of from about 4.4 to about 9.4.

47. The method of claim 45, wherein said dye is selected from indophenols, indoanilines, and indamines.

48. The method of claim 47, wherein the dye is selected from the group consisting of 2,6-dichlorophenol-indophenol and thionin.

49. The method of claim 43, wherein said neutralizer is selected from alkali metal sulfites, alkali metal bisulfites, and a mixture of alkali metal sulfites and alkali metal bisulfites.

50. A test kit for determining the neutralization of formaldehyde in an aqueous solution initially containing formaldehyde by exposure to sulfite ions, said test kit comprising:

a neutralizer that produces sulfite ions in aqueous solution; and
  a test strip including a dye capable of exhibiting a color change in the presence of a stoichiometric excess of sulfite ions over the amount of formaldehyde in the solution.

51. The test kit of claim 50, wherein said dye has a reduction potential at neutral pH of 0.074 volt or greater.

52. The test kit of claim 50, wherein said dye is capable of exhibiting said color change at a pH of from about 4.4 to about 9.4.

53. The test kit of claim 51, wherein said dye is selected from indophenols, indoanilines, and indamines.

54. The test kit of claim 53, wherein said dye is selected from the group consisting of 2,6-dichlorophenol-indophenol and thionin.

55. The test kit of claim 50, wherein said test strip further includes a buffer capable of providing a pH of from about 6.0 to about 8.0.

56. The method of claim 50, wherein said neutralizer is selected from alkali metal sulfites, alkali metal bisulfites, and a mixture of alkali metal sulfites and alkali metal bisulfites.

57. The test kit of claim 50, wherein said test strip if formed of a bibulous material with a polystyrene backing.

* * * * *